US012357381B2

(12) United States Patent
Dickhans et al.

(10) Patent No.: US 12,357,381 B2
(45) Date of Patent: Jul. 15, 2025

(54) MICROWAVE ABLATION DEVICES

(71) Applicant: Covidien LP, Mansfield, MA (US)

(72) Inventors: William J. Dickhans, Longmont, CO (US); Jiagui Li, Shanghai (CN); Zhiwei Lin, Shanghai (CN); Darion R. Peterson, Longmont, CO (US); Wei Zhang, Shanghai (CN)

(73) Assignee: Covidien LP, Mansfield, MA (US)

( * ) Notice: Subject to any disclaimer, the term of this patent is extended or adjusted under 35 U.S.C. 154(b) by 1015 days.

(21) Appl. No.: 16/973,660

(22) PCT Filed: Jul. 2, 2018

(86) PCT No.: PCT/CN2018/094069
§ 371 (c)(1),
(2) Date: Dec. 9, 2020

(87) PCT Pub. No.: WO2020/006661
PCT Pub. Date: Jan. 9, 2020

(65) Prior Publication Data
US 2021/0251688 A1  Aug. 19, 2021

(51) Int. Cl.
*A61B 18/18* (2006.01)
*A61B 18/00* (2006.01)

(52) U.S. Cl.
CPC .............. *A61B 18/1815* (2013.01); *A61B 2018/00577* (2013.01); *A61B 2018/00642* (2013.01);
(Continued)

(58) Field of Classification Search
CPC ................................. A61B 18/1815
See application file for complete search history.

(56) References Cited

U.S. PATENT DOCUMENTS 9,247,992 B2    2/2016   Ladtkow et al.
2004/0049254 A1 3/2004   Longo
(Continued)

FOREIGN PATENT DOCUMENTS

CN    104042339 A    9/2014
CN    105073052 A    11/2015
(Continued)

OTHER PUBLICATIONS

Extended European Search Report dated Jan. 18, 2022, issued in corresponding EP Appln. No. 18925644, 9 pages.
(Continued)

*Primary Examiner* — Sean W Collins
(74) *Attorney, Agent, or Firm* — Carter, DeLuca & Farrell LLP

(57) ABSTRACT

A microwave ablation device includes a cable assembly, a feedline, and a transmission line. The cable assembly is configured to connect to an energy source. The feedline is in electrical communication with the cable assembly and includes a first temperature sensor. The first temperature sensor is disposed at a first axial location along a length of the feedline and is configured to sense a temperature at the first axial location. The first temperature sensor extends along the length of the feedline. The transmission line extends from the first temperature sensor and is disposed parallel and in contact with an outer conductor of the feedline.

8 Claims, 9 Drawing Sheets

(52) U.S. Cl.
CPC ............... *A61B 2018/00684* (2013.01); *A61B 2018/00714* (2013.01); *A61B 2018/00797* (2013.01); *A61B 2018/00821* (2013.01); *A61B 2018/00898* (2013.01); *A61B 2018/1892* (2013.01)

(56) References Cited

U.S. PATENT DOCUMENTS

| | | | |
|---|---|---|---|
| 2010/0268219 A1* | 10/2010 | Ormsby | A61B 18/18 606/33 |
| 2012/0203100 A1 | 8/2012 | Weiss et al. | |
| 2012/0232544 A1 | 9/2012 | Willyard et al. | |
| 2014/0276739 A1* | 9/2014 | Brannan | A61B 34/25 606/33 |
| 2016/0030111 A1* | 2/2016 | Ladtkow | A61B 18/1815 606/33 |
| 2016/0051221 A1 | 2/2016 | Dickhans et al. | |
| 2018/0008345 A1 | 1/2018 | Williams et al. | |

FOREIGN PATENT DOCUMENTS

| | | |
|---|---|---|
| CN | 106420047 A | 2/2017 |
| CN | 107224325 A | 10/2017 |
| CN | 108042201 A | 5/2018 |
| JP | H05293086 A | 11/1993 |

OTHER PUBLICATIONS

International Search Report and Written Opinion dated Mar. 27, 2019, issued in corresponding international appln. No. PCT/CN2018/094069, 12 pages.

* cited by examiner

MICROWAVE ABLATION DEVICES

CROSS-REFERENCE TO RELATED APPLICATION

This application is a National Stage Application of PCT Application Serial No. PCT/CN2018/094069 under 35 USC § 371 (a), filed Jul. 2, 2018, the disclosure of the above-identified application is hereby incorporated by reference in its entirety.

BACKGROUND

Technical Field

The present disclosure relates to microwave ablation devices suitable for use in tissue ablation applications.

Discussion of Related Art

Treatment of certain diseases requires the destruction of malignant tissue growths, for example, tumors. Electromagnetic radiation can be used to heat and destroy tumor cells. Treatment may involve inserting ablation probes into tissue where cancerous tumors have been identified. Once the probes are positioned, electromagnetic energy is passed through the probes into surrounding tissue.

In the treatment of diseases such as cancer, certain types of tumor cells have been found to denature at elevated temperatures that are slightly lower than temperatures normally injurious to healthy cells. Known treatment methods, such as hyperthermia therapy, heat diseased cells to temperature at which irreversible cell destruction occurs. These methods involve applying electromagnetic radiation to heat or ablate tissue.

Electrosurgical devices utilizing electromagnetic radiation have been developed for a variety of uses and applications. Typically, devices for use in ablation procedures include a power generation source, for example, a microwave or radio frequency (RF) electrosurgical generator that functions as an energy source, and a microwave ablation instrument (e.g., a microwave ablation probe having an antenna assembly) for directing energy to the target tissue. The generator and microwave ablation instrument are typically operatively coupled by a cable assembly having a plurality of conductors for transmitting energy from the generator to the instrument, and for communicating control, feedback and identification signals between the instrument and the generator.

A common mechanism used to monitor the temperature of a probe during tissue ablation application is a temperature sensor, such as a thermocouple. Generally, thermocouples consist of two dissimilar metal wires, joined at one end, that are selected to correlate with a targeted temperature range. Thermocouples measure a voltage change between the wires to be used to precisely calculate the temperature of the probe.

Because of the small temperature difference between the temperature required for denaturing malignant cells and the temperature normally injurious to healthy cells, a known heating pattern and precise temperature monitoring are needed. For example, precise temperature control may lead to more predictable temperature distribution during tumor cell eradication, while minimizing damage to surrounding healthy cells.

SUMMARY

According to an embodiment of the present disclosure, a microwave ablation device includes a cable assembly, a feedline, and a transmission line. The cable assembly is configured to connect to an energy source. The feedline is in electrical communication with the cable assembly and includes a first temperature sensor. The first temperature sensor is disposed at a first axial location of the feedline and is configured to sense a temperature at the first axial location. The first temperature sensor extends along a length of the feedline. The transmission line extends from the first temperature sensor and is disposed parallel and in contact with an outer conductor of the feedline.

In embodiments, the feedline may further include a balun disposed on the outer conductor. Additionally, the microwave ablation device may further include an antenna assembly. The antenna assembly may be electrically connected to the feedline and be positioned distal to the balun. The antenna assembly may include a proximal radiating section, a distal radiating section, and a feedgap. The proximal radiating section may be disposed proximate to the balun. The distal radiating section may be disposed distal to the proximal radiating section. The feedgap may be disposed between the proximal radiating section and the distal radiating section.

In embodiments, the first temperature sensor may be disposed proximate to the balun.

In embodiments, the first temperature sensor may be disposed distal to the balun and proximal to the feedgap.

In embodiments, the feedline may further include an inner conductor, an outer conductor extending coaxially with the inner conductor, and a dielectric material disposed between the inner conductor and the outer conductor.

In embodiments, the first temperature sensor may be disposed over the outer conductor.

In embodiments, the feedline may further include a second temperature sensor. The second temperature sensor may be disposed at a second axial location along the length of the feedline and be configured to sense a temperature at the second axial location. The first temperature sensor may be disposed proximal to the second temperature sensor.

In embodiments, the feedline may further include a plurality of second temperature sensors. Each of the second temperature sensors may be disposed at a different axial location along the length of the feedline and configured to sense a temperature at each of the different axial locations. The first temperature sensor may be located proximal to the plurality of second temperature sensors. The plurality of second temperature sensors may be arranged in an array.

Also provided in accordance with the present disclosure is a feedline including an inner conductor, an outer conductor, a dielectric material, and a first temperature sensor. The outer conductor is disposed coaxially with the inner conductor, wherein the dielectric material is disposed between the inner conductor and outer conductor. The first temperature sensor is disposed at a first axial location of the outer conductor and extends along a length of the outer conductor. The first temperature sensor is configured to sense a temperature at the first axial location.

In embodiments, the first temperature sensor may be disposed over the outer conductor.

In embodiments, the feedline may further include a second temperature sensor. The second temperature sensor may be disposed at a second axial location along the length of the outer conductor and be configured to sense a temperature at the second axial location. The first temperature sensor may be disposed proximal to the second temperature sensor.

In embodiments, the feedline may further include a plurality of second temperature sensors with each being disposed at different axial locations along the length of the outer conductor and configured to sense a temperature at each of the different axial locations. The first temperature sensor may be positioned proximal to the plurality of second temperature sensors. The plurality of the second temperature sensors may be arranged in an array.

In another aspect of the present disclosure, a method of manufacturing a feedline is provided. A feedline is formed by coating a conductive wire with a dielectric material, placing a conductive material over the dielectric material, and positioning a first temperature sensor over the conductive material.

Some methods may further include positioning a second temperature sensor over the conductive material. The first temperature sensor may be proximal to the second temperature sensor.

Some methods may further include positioning a plurality of second temperature sensors over the conductive material. The first temperature sensor may be proximal to the plurality of second temperature sensors.

BRIEF DESCRIPTION OF THE DRAWINGS

Objects and features of the present disclosure will become apparent to those of ordinary skill in the art when descriptions of various embodiments thereof are read with reference to the accompanying drawings, of which.

DETAILED DESCRIPTION

Figure 1:
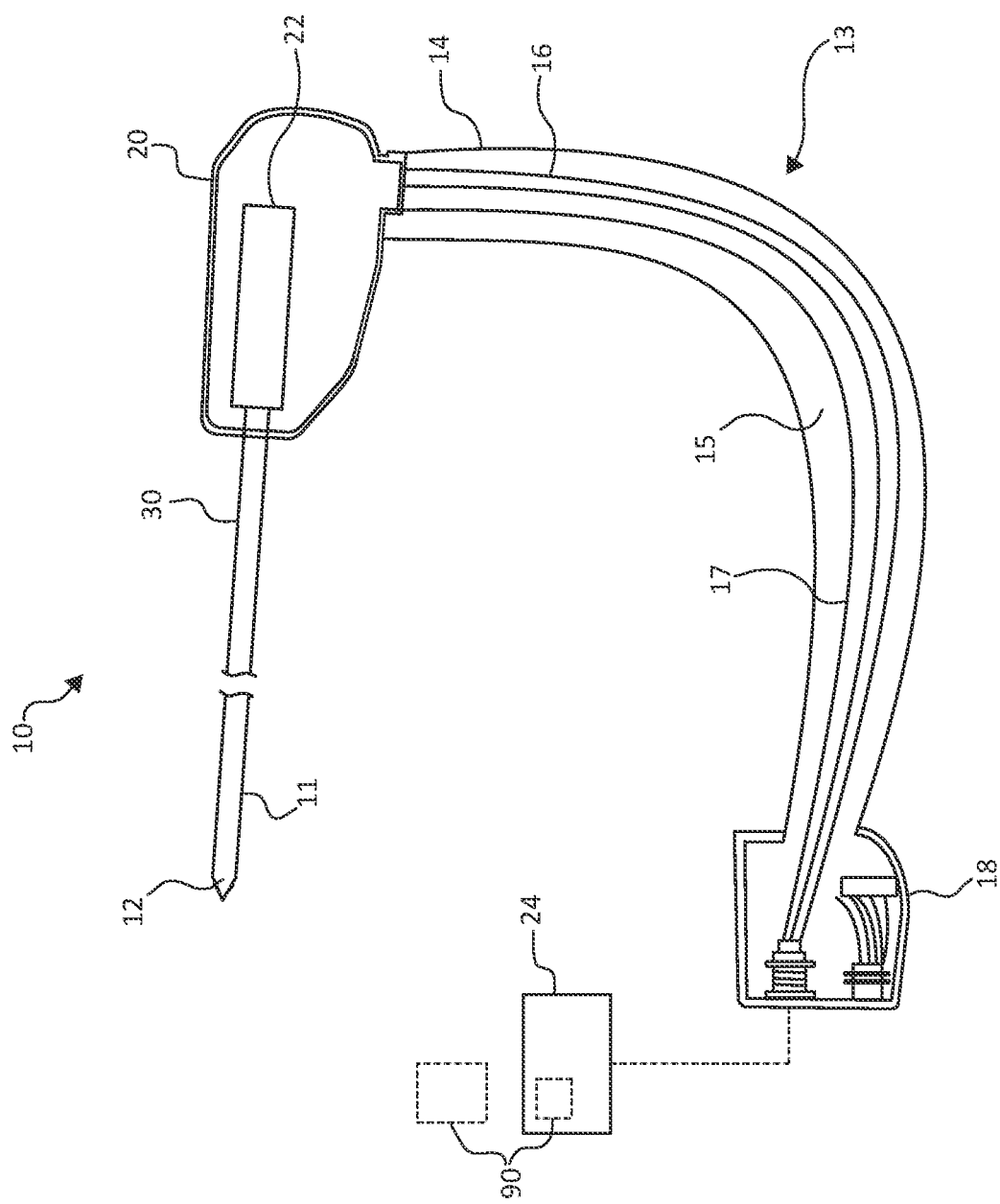
FIG. 1 is a schematic diagram of a microwave ablation system in accordance with an illustrative embodiment of the present disclosure.

The present disclosure is directed to a microwave ablation device including a probe assembly with a temperature sensor and methods of manufacturing the probe assembly. In particular, the present disclosure provides a microwave ablation probe which includes a temperature sensor positioned upon and extending coaxially with the feedline. In this way, the temperature sensor may be placed more accurately within the probe to thereby provide more reliable temperature readings. As a result, the probe assembly may be more precisely controlled during an ablation procedure.

Hereinafter, embodiments of the microwave ablation device of the present disclosure are described with reference to the accompanying drawings. Like reference numerals may refer to similar or identical elements throughout the description of the figures. As shown in the drawings and as used in this description, and as is traditional when referring to relative positioning on an object, the term "proximal" refers to the portion of the apparatus or component thereof, closer to a clinician and the term "distal" refers to the portion of the apparatus, or component thereof, farther from the clinician.

Figure 2:
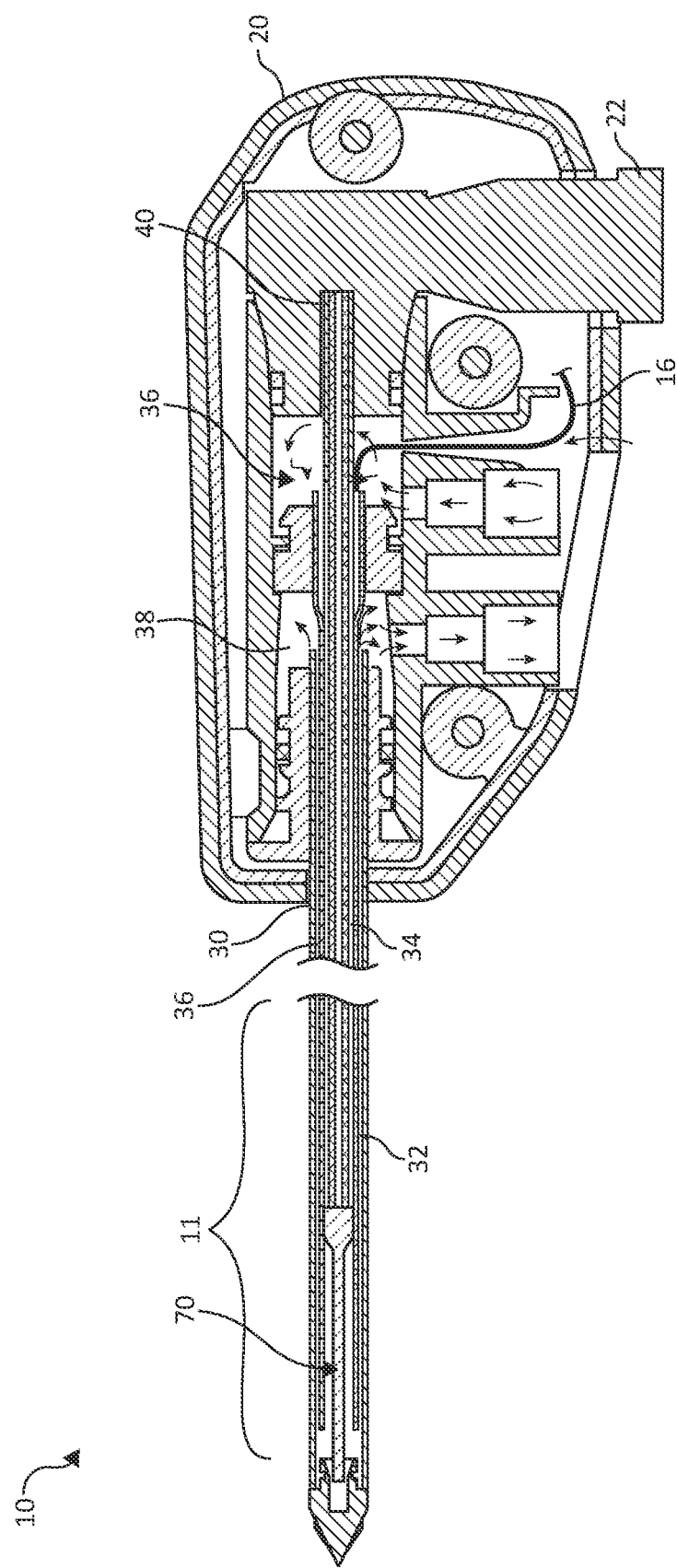
FIG. 2 is an enlarged, longitudinal cross-sectional view of the probe assembly and a housing assembly of the embodiment shown in FIG. 1.

With reference to FIGS. 1 and 2, various views of a microwave ablation system are provided. The microwave ablation system includes a microwave ablation device 10 and a generator 24. Device 10 generally includes a probe assembly 11, a cable assembly 13, a connector assembly 18, and a handle assembly 20. The probe assembly 11 is operably coupled by the cable assembly 13 to the connector assembly 18.

The connector assembly 18 is a cable connector suitable to operably connect the microwave ablation device 10 to the microwave generator 24. The connector may house a memory (e.g., an EEPROM) (not separately shown in FIG. 1) storing a variety of information regarding the cable assembly 13 and the microwave ablation device 10. For example, the memory may include identification information that can be used by the microwave generator 24 to ensure that only properly identified microwave ablation devices are connected thereto. In addition, the memory may store operating parameters of the microwave ablation device 10 (for example, time, power, and dosage limits), cable compensation parameters of the cable assembly 13, and information regarding the usage of the microwave ablation device 10 or the cable assembly 13. Still further, the connector assembly 18 may include sensor electronics (not separately shown in FIG. 1) related to radiometry and temperature sensing as described below.

The cable assembly 13 may include a tubular member 14, which defines a lumen 15 through which a transmission line 16 and an electrical wire 17 pass. The transmission line 16 may be any suitable, flexible transmission line, and particularly a coaxial cable including an inner conductor, and an outer conductor coaxially surrounding a dielectric material. The electrical wire 17 may be any suitable electrical wire.

In an embodiment, usage monitoring may enable limiting re-use of the microwave ablation device 10 beyond a certain number of energizations or a single use of the device and/or the sensed temperatures may be analyzed. In this regard, a temperature monitoring system 90 (FIG. 1) may be included as part of the microwave generator 24. In another example, the temperature monitoring system 90 may be separate from the microwave generator 24 and may be configured to provide audible or visual feedback to the clinician during use of the microwave ablation device 10. The temperature monitoring system 90 may be utilized with the probe assembly 11 to observe/monitor tissue temperatures in or adjacent an ablation zone.

Figure 3:
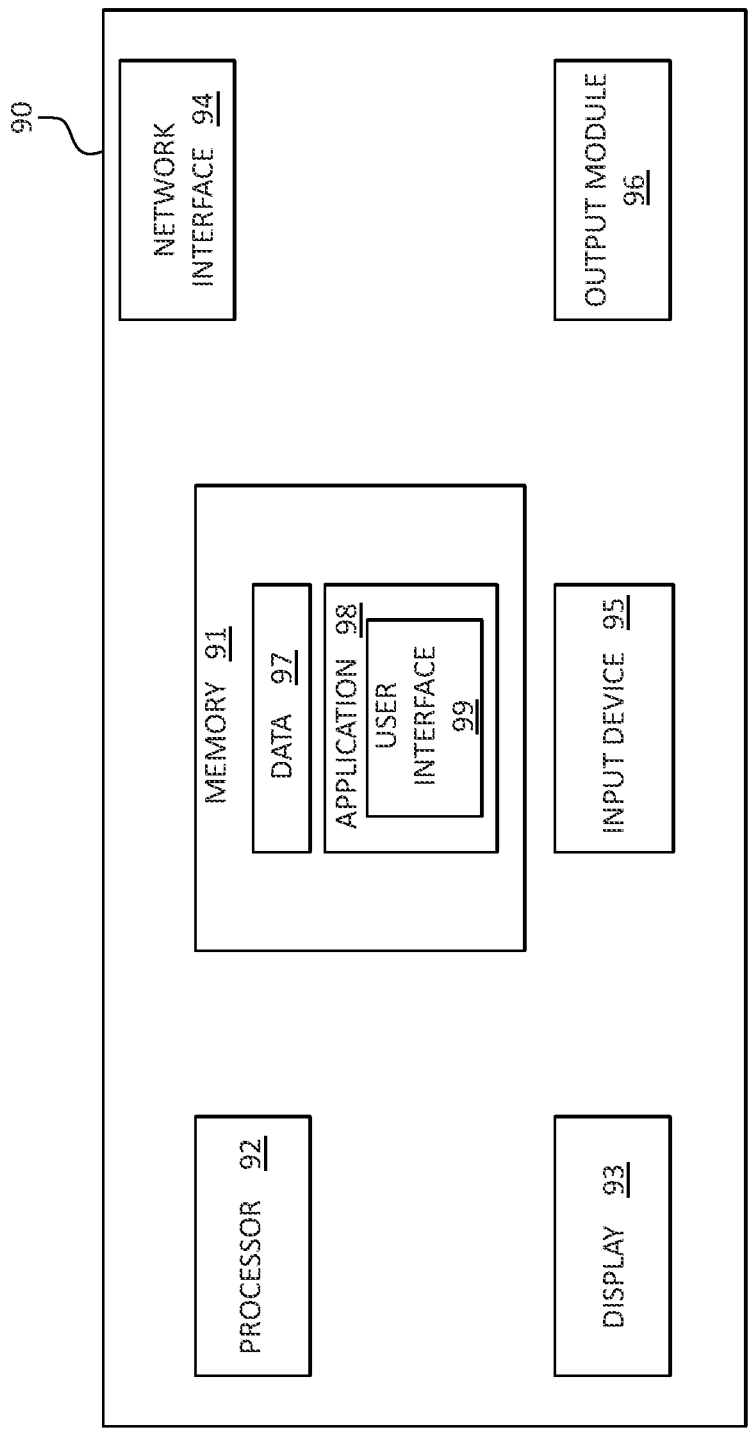
FIG. 3 is a block diagram of a temperature monitoring system, in accordance with an illustrative embodiment of the present disclosure.

Referring now to FIG. 3, the temperature monitoring system 90 can be, for example, a radiometry system, a thermocouple based system or any other tissue temperature monitoring system known in the art. In the embodiment illustrated in FIG. 3, the temperature monitoring system 90 is configured as a computing device including a memory 91, a processor 92, display 93, a network interface 94, an input device 95, and/or an output module 96. The temperature monitoring system 90 is configured to provide tissue temperature and ablation zone information to the microwave generator 24.

The memory 91 includes any non-transitory computer-readable storage media for storing data and/or software that is executable by the processor 92 and which controls the operation of the microwave ablation device 10. In an embodiment, the memory 91 stores data 97 related to ablation zone configurations, previously gathered through empirical testing, as one or more data look-up tables. Alternatively or in addition to the one or more solid-state storage devices, the memory 91 may include one or more mass storage devices connected to the processor 92 through a mass storage controller (not shown) and a communications bus (not shown). Although the description of computer-readable media contained herein refers to a solid-state storage, it should be appreciated by those skilled in the art that computer-readable storage media can be any available media that can be accessed by the processor 92. That is, computer readable storage media includes non-transitory, volatile and non-volatile, removable and non-removable media implemented in any method or technology for storage of information such as computer-readable instructions, data structures, program modules or other data. For example, computer-readable storage media includes RAM, ROM, EPROM, EEPROM, flash memory or other solid state memory technology, CD-ROM, DVD, Blu-Ray or other optical storage, magnetic cassettes, magnetic tape, magnetic disk storage or other magnetic storage devices, or any other medium which can be used to store the desired information and which can be accessed by the microwave ablation device 10.

The memory 91 may store an application 98. The application 98 may, when executed by the processor 92, cause the processor 92 to correlate the tissue temperature and ablation zone data gathered by temperature sensors (for example, a first temperature sensor 50 and/or a second temperature sensor(s) 52 in the probe assembly 11) with the data 97 stored in the memory 91. In another embodiment, the application 98, when executed by the processor 92, may cause the temperature monitoring system 90 to calculate a proposed course of treatment, a power setting, and the duration or number of serial energy applications that will achieve a desired ablation zone effective for treating the target tissue. For example, the clinician may enter the size of the target tissue into the temperature monitoring system 90, and the system 90 provides instruction for the treatment of the target tissue. In another embodiment, the application 98, when executed by the processor 92, causes the system 90 to access the data look-up tables stored in the memory 91, and to compare the tissue temperatures and/or ablation zone temperatures sensed by the first temperature sensor 50 (FIG. 5) and/or the second temperature sensor(s) 52 (FIG. 8) with the stored ablation zone configuration. Command signals may be sent automatically to adjust the microwave energy output to the microwave ablation device 10. In another embodiment, a manual adjustment protocol may be utilized to control the microwave energy output to the microwave ablation device 10, for example, to cause an indicator to provide an output (for example, visual, audio and/or tactile indications) to the clinician when a particular tissue temperature and/or ablation zone temperature is matched to a corresponding ablation zone configuration.

In another embodiment, the application 98 may, when executed by the processor 92, cause the display 93 to present the user interface 99. The network interface 94 may be configured to connect to a network such as a local area network (LAN) consisting of a wired network and/or a wireless network, a wide area network (WAN), a wireless mobile network, a Bluetooth network, and/or the internet. The input device 95 may be any device by means of which a user may interact with the microwave ablation device 10, such as, for example, a mouse, keyboard, foot pedal, touch screen, and/or voice interface. The output module 96 may include any connectivity port or bus, such as, for example, parallel ports, serial ports, universal serial busses (USB), or any other similar connectivity port known to those skilled in the art.

With reference to FIG. 2, the probe assembly 11 includes an outer tubular member 30, an inner tubular member 32, a feedline 40, an antenna assembly 70, a temperature sensor 50 (FIG. 4), and a distal tip 12. The outer tubular member 30 and the inner tubular member 32 may be formed of any suitable non-electrically-conductive material, such as, for example, polymeric or ceramic material. In an embodiment, the inner tubular member 32 is coaxially disposed around the feedline 40 and defines a first lumen 34 therebetween, and the outer tubular member 30 is coaxially disposed around the inner tubular member 32 and defines a second lumen 36 therebetween. In an embodiment, the distal tip 12 may be a trocar.

Figure 4:
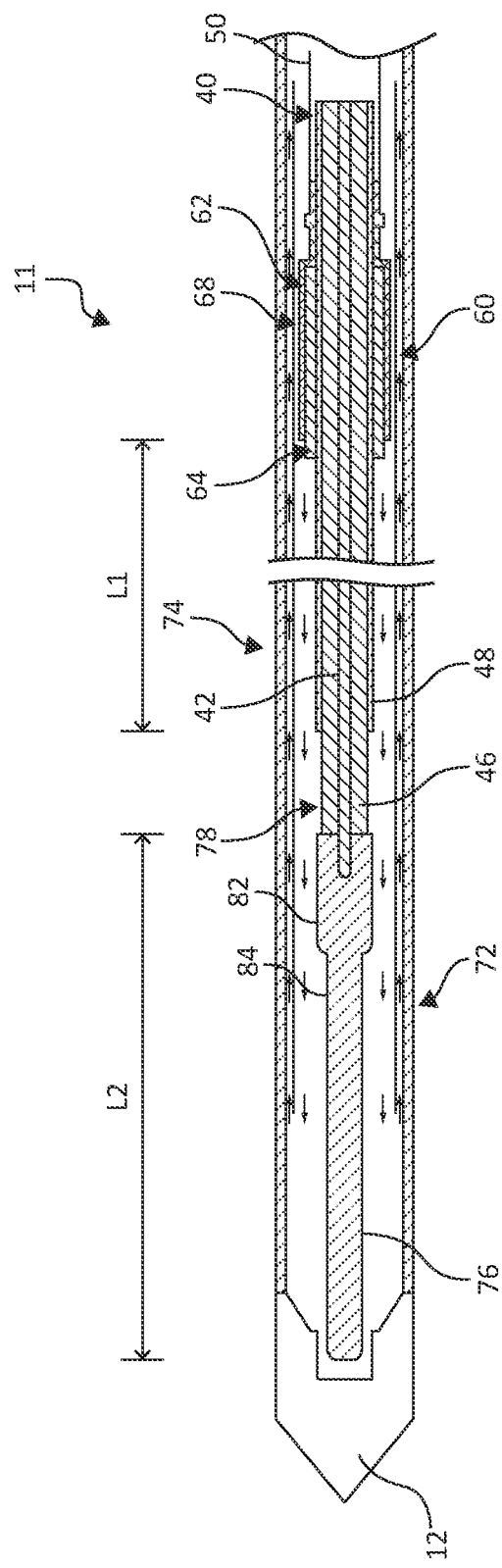
FIG. 4 is a longitudinal cross-sectional, partial view of a distal portion of a probe assembly in accordance with an embodiment of the present disclosure.

Turning now to FIG. 4, in an embodiment of a portion of the probe assembly 11, an antenna assembly 70 is included having a first radiating portion (for example, distal radiating section 72) and a second radiating portion (for example, proximal radiating section 74). The antenna assembly 70 includes the proximal radiating section 74 having a length "L1," the distal radiating section 72 including an electrically-conductive element 76 having a length "L2," and a feedgap 78 disposed therebetween. In an embodiment, the proximal radiating section 74 may have the length "L1" in a range of from about 0.050 inches (1.27 mm) to about 0.50 inches (12.7 mm). The electrically-conductive element 76 may be formed of any suitable electrically-conductive material, for example, metal such as stainless steel, aluminum, titanium, copper, or the like. In an embodiment, the electrically-conductive element 76 may have the length "L2" in a range from about 0.15 inches (3.81 mm) to about 0.10 inches (2.54 mm). In an embodiment, the electrically-conductive element 76 has a stepped configuration, such that the outer diameter of a distal portion 84 thereof is less than the outer diameter of a proximal portion 82 thereof. The antenna assembly 70 is operably coupled by the feedline 40, which is described in more detail below, to a transition assembly 22 shown in FIG. 1. The transition assembly 22 is adapted to transmit microwave energy, from the cable assembly 13 to the feedline 40.

Figure 5:
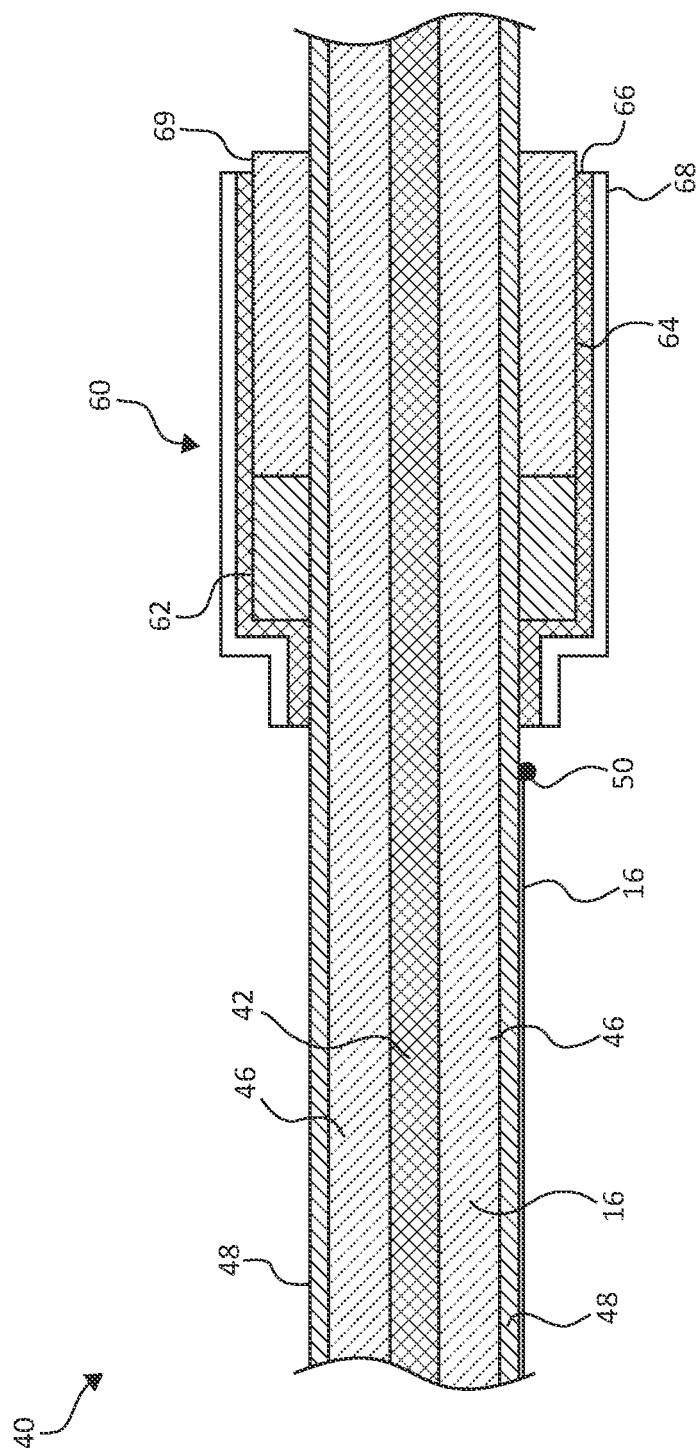
FIG. 5 is an enlarged, longitudinal cross-sectional view of a portion of a feedline of a probe assembly depicting a temperature sensor in accordance with an embodiment of the present disclosure.

The feedline 40 may be a coaxial cable or any other type of suitable transmission line. In an embodiment, as shown in FIG. 5, the feedline 40 includes an inner conductor 42, an outer conductor 48 extending coaxially with to be disposed around the inner conductor 42, and a dielectric material 46 disposed therebetween. Additionally, the feedline 40 includes a first temperature sensor 50 disposed on the coaxial cable 40. The inner conductor 42 and the outer conductor 48 may be formed from any suitable electrically-conductive material. In an embodiment, the inner conductor 42 is formed from a first electrically-conductive material (for example, stainless steel) and the outer conductor 48 is formed from a second electrically-conductive material (for example, copper). Electrically-conductive materials used to form the feedline 40 may be plated with other materials, for example, other conductive materials, such as gold or silver, to improve their properties, for example, to improve conductivity, decrease energy loss, etc. The dielectric material 46 may be formed from any suitable dielectric material, for example, polyethylene, polyethylene terephthalate, polyimide or polytetrafluoroethylene (PTFE).

The feedline 40 may have any suitable length defined between its proximal and distal ends. In accordance with an embodiment of the present disclosure, the feedline 40 is coupled at its proximal end to the transition assembly 22 (FIG. 2) and coupled at its distal end to the antenna assembly 70 (FIG. 4). The feedline 40 is disposed at least in part within the inner tubular member 32 (FIG. 2). In an embodiment, the inner conductor 42 of the feedline 40 extends past the distal end of both the dielectric material 46 and the outer conductor 48 and into the proximal portion 82 of the antenna assembly 70. An opening 80, formed in the proximal portion 82 approximately at 90 degrees to the inner conductor 42 allows for solder, a set screw, or other securing mechanisms to physically secure the electrically conductive element 76 to the inner conductor 42 and therewith the feedline 40 of the microwave ablation device 10.

In an embodiment, the outer conductor 48 may be braided, for example, including three or more strands intertwined. While the outer conductor 48 is described as a braid, the actual construction is not so limited and may include other formations of outer conductors of coaxial cables as would be understood by those of ordinary skilled in the art. The feedline 40 may incorporate one or more aspects of the ablation system described in U.S. Pat. No. 9,247,992 to Ladtkow et al. entitled "Microwave Ablation Catheter and Method of Utilizing the Same," the entire contents of which are incorporated herein by reference.

The probe assembly 11 may include a balun 60 disposed proximal to and spaced apart a suitable distance from the feedgap 78. The balun 60 generally includes a balun short 62 and a balun insulator 64, which both couple the balun 60 to the outer conductor 48 of the feedline 40. The balun short 62 may be formed as a single structure and electrically coupled to the outer conductor 48 of the feedline 40 by a suitable manner of electrical connection, for example, soldering, welding or laser welding. Also, the balun short 62 may be formed by any suitable electrically-conductive materials, for example, copper, gold, silver or other conductive metals or metal alloys. In an embodiment, the balun short 62 has a generally ring-like or truncated tubular shape. In other embodiments, the balun 60 is devoid of a balun short. The size and shape of the balun short 62 may be varied from the configuration depicted in FIG. 5. In an embodiment, the balun 60 may be a ¼ λ balun or a ¾ λ balun.

FIGS. 4 and 5 further depict the balun insulator 64 extending coaxially with and disposed over the outer conductor 48 of the feedline 40. The balun insulator 64 may be formed of any suitable insulative material, including, but not limited to, ceramics, water, mica, polyethylene, polyethylene terephthalate, polyimide, polytetrafluoroethylene (PTFE) (for example, Teflon®), glass, metal oxides or other suitable insulator, and may be formed in any suitable manner. In an embodiment, the balun insulator 64 may be a dielectric sleeve. The balun insulator 64 may be grown, deposited or formed by any other suitable technique. In an embodiment, the balun insulator 64 may be formed from a material with a dielectric constant (k) in the range of about 1.7 to about 10.

A tubing member 68 including an inner layer of an electrically-conductive material 66 is illustrated. In an embodiment, the tubing member 68 may be a heat shrink tubing member, which has the capability of responding to heat and binding around an object. The heat shrink tubing member may be a thermoplastic. The electrically-conductive material 66 may be formed of any suitable electrically-conductive material, for example, metallic material. In an embodiment, the metallic material of electrically-conductive layer 66 is formed of a silver ink deposited or layered on an interior surface of the tubing member 68. The tubing member 68 may have a length from about 1 inch (25.4 mm) to about 3 inches (76.2 mm) in length. However, the shape and size of the tubing member 68 and the balun insulator 64 may be varied from the configuration depicted in FIGS. 4 and 5 without departing from the scope of the present disclosure. After the application of thermal energy to the tubing member 68, the tubing member 68 shrinks causing the electrically-conductive material 66 to contact with the balun short 62 and a portion of the balun insulator 64. For example, a portion of the balun insulator 64 may extend distally beyond the distal end of the tubing member 68 and the electrically-conductive layer 66, to create a gap 69. The gap 69 improves the microwave performance of the probe assembly 11 and can assist in achieving a desired ablation pattern. More specifically, the gap 69 ensures adequate coupling of microwave energy from the proximal radiating section 74 into the balun 60, improving the performance of the balun 60 over a wide range of tissue dielectric conditions.

The balun 60 is connected to the antenna assembly 70. In operation, microwave energy having a wavelength lambda (λ) is transmitted through the antenna assembly 70 and radiated into the surrounding medium, for example, tissue. The length of the antenna for efficient radiation may be dependent on the effective wavelength, Neff, which is dependent upon the dielectric properties of the treated medium. The antenna assembly 70 through which microwave energy is transmitted at a wavelength λ may have differing effective wavelengths, Neff, depending upon the surrounding medium, e.g., liver tissue as opposed to breast tissue, lung tissue, kidney tissue, etc.

The first temperature sensor 50 is disposed on the feedline 40. In particular, the first temperature sensor 50 is coupled to the outer conductor 48 and extends generally along a longitudinal axis of the feedline 40 and terminates under the balun 60 and is held in place under the balun 60 using potting material, such as, for example, a heat resistant epoxy. The first temperature sensor 50 is in contact and parallel with an outer surface of the outer conductor 48 of the feedline 40. In an embodiment, the first temperature sensor 50 is a thermocouple and the transmission 16 is a thermocouple wire. In embodiments, the first temperature sensor 50 and the transmission 16 may be monolithically formed. The thermocouple wire 16 may be a two lead wire thermocouple wire, for example, and may be made up of an insulated (anodized) side-by-side Constantine wire and copper wire.

Figure 6:
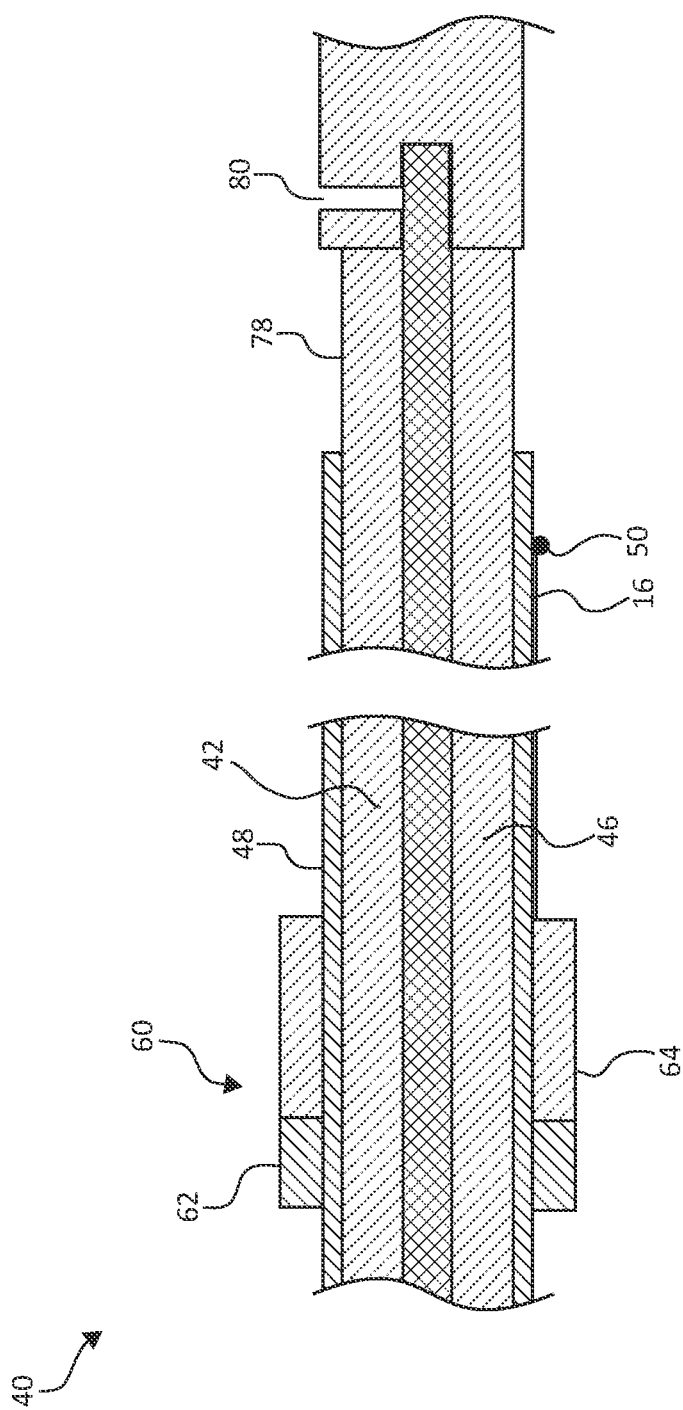
FIG. 6 is an enlarged, longitudinal cross-sectional view of a portion of a feedline of a probe assembly depicting a temperature sensor in accordance with another embodiment of the present disclosure.

As illustrated in FIG. 5, the first temperature sensor 50 may be disposed at a location along the length of the feedline 40 that is proximate to the axial location of the balun short 62. The first temperature sensor 50 may be received or potted within a hole (not explicitly shown) defined in the balun short 62. In one embodiment, the first temperature sensor 50 may be proximal to the axial location of the balun short 62 (FIG. 5). In another embodiment, the first temperature sensor 50 may be distal to the axial location of the balun short 62 (not shown). In a further embodiment, the first temperature sensor 50 may be distal to the axial location of the balun insulator 64 (FIG. 6). For example, in an embodiment illustrated in FIG. 6, the first temperature sensor 50 is located between the balun insulator 64 and the feedgap 78.

By disposing the first temperature sensor 50 closer to the balun short 62, the temperature of the balun short 62 can be more accurately sensed to thereby permit the first temperature sensor 50 to act as a safety indicator. For instance, in response to the first temperature sensor 50 detecting a temperature that exceeds a pre-determined threshold temperature (for example, 45° C.), which can lead to unintended cell death in tissue, the system 10 may cause the generator 24 to shut down or provide an alarm as the sensed temperature approaches the pre-determined threshold temperature, thus preventing injury to the patient.

In accordance with another embodiment, the axial location of the first temperature sensor 50 along the feedline 40 may be at approximately 0.8 inch (20.32 mm), 1.0 inch (25.4 mm), 1.2 inches (30.48 mm), and 1.4 inches (35.56 mm) from the distal tip 12 of the microwave ablation device 10. The distal end of the first temperature sensor 50 may be located a specified distance from the distal radiating section 72 that provides the most accurate temperature measurements.

Figure 7:
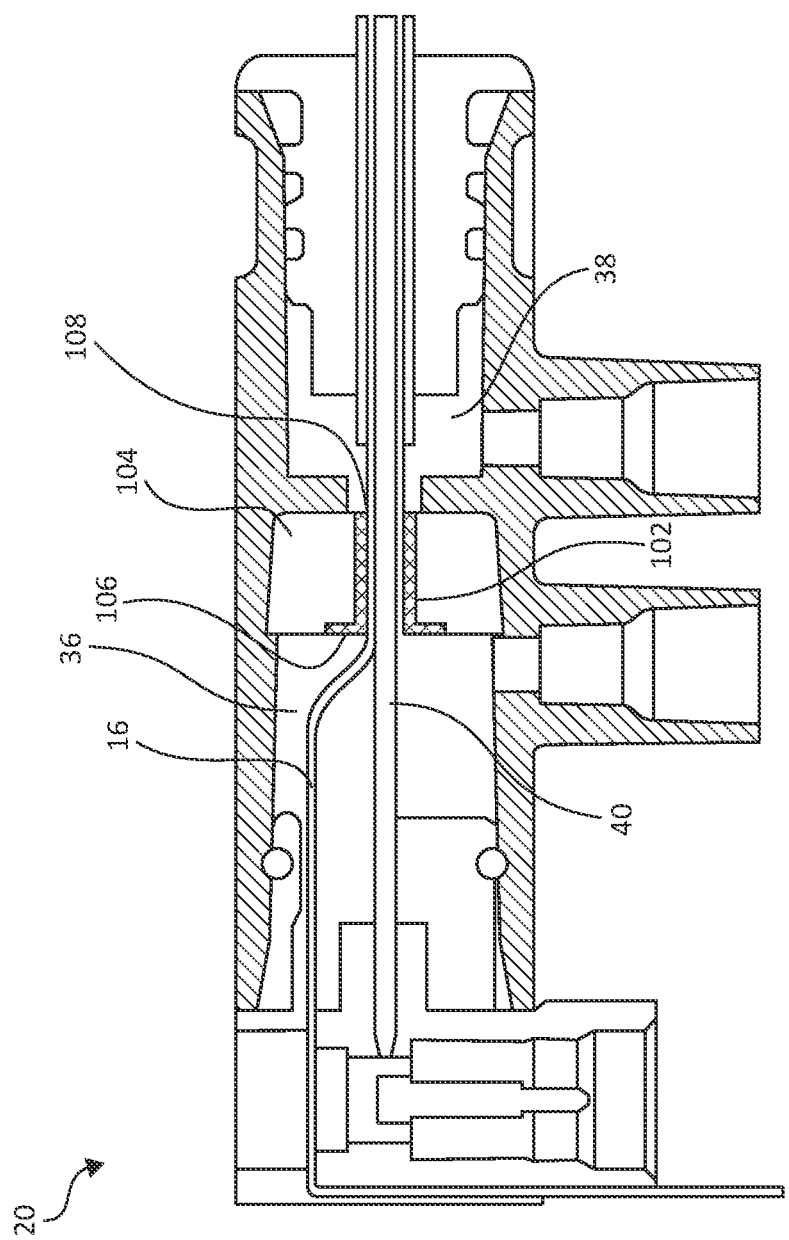
FIG. 7 is a partial cross-sectional view of a microwave ablation antenna assembly according to aspects of the present disclosure.

With reference to FIG. 7, an embodiment of the handle assembly 20 includes an inflow tube insert 102 received within a hub divider 104. The inflow tube insert 102 includes a flange 106 formed on one end. The flange 106 forms a surface upon which fluid in an inflow chamber 36 acts, and when the inflow chamber 36 is pressurized, compresses the hub divider 104 forming a water tight seal. As a result of this seal between the flange 106 and the hub divider 104, the circulated fluid is forced into the spacing between the inflow tube insert 102 and the feedline 40. After flowing to the distal portion of the microwave ablation device 10, the fluid is released into an outflow chamber 38.

The inflow tube insert 102 is disposed about a proximal end portion of the feedline 40. The transmission 16 (e.g., the proximal portion of the first temperature sensor 50) extends through a longitudinally-extending channel 108 defined through the inflow tube insert 102 and runs parallel with and along an outer surface of the outer conductor of the feedline 40. The channel 108 of the inflow tube insert 102 has a diameter large enough to accommodate both the feedline 40 and the transmission 16 while providing a space between an inner annular surface thereof and the transmission 16.

Figure 8:
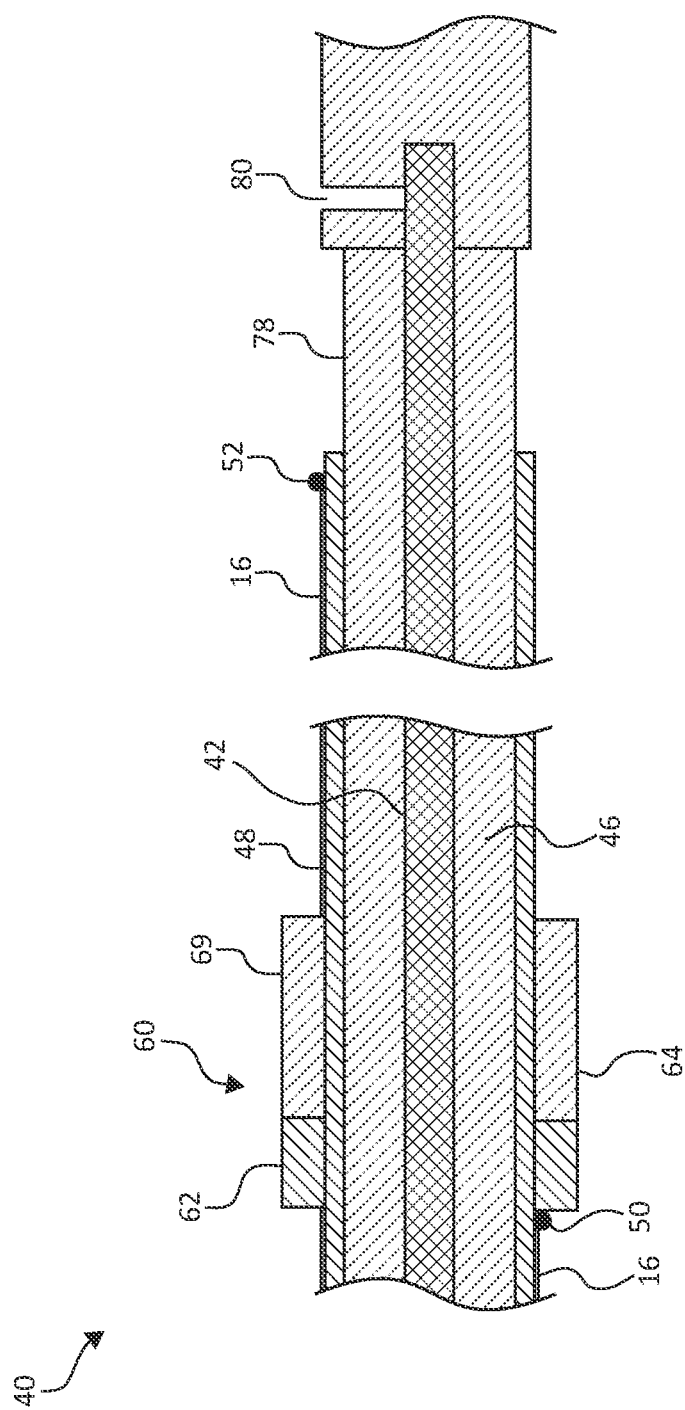
FIG. 8 is an enlarged, longitudinal cross-sectional view of a portion of a feedline of a probe assembly depicting two temperature sensors in accordance with an embodiment of the present disclosure.

FIG. 8 depicts a further embodiment of the present disclosure in which more than one temperature sensor is included. Here, the device 10 includes a second temperature sensor 52. The first temperature sensor 50 and the second temperature sensor 52 are disposed on the feedline 40 at different locations to sense the temperatures at different axial positions along the length of the feedline 40 simultaneously, for example, adjacent to the balun 60 and adjacent to the feedgap 78.

Figure 9:
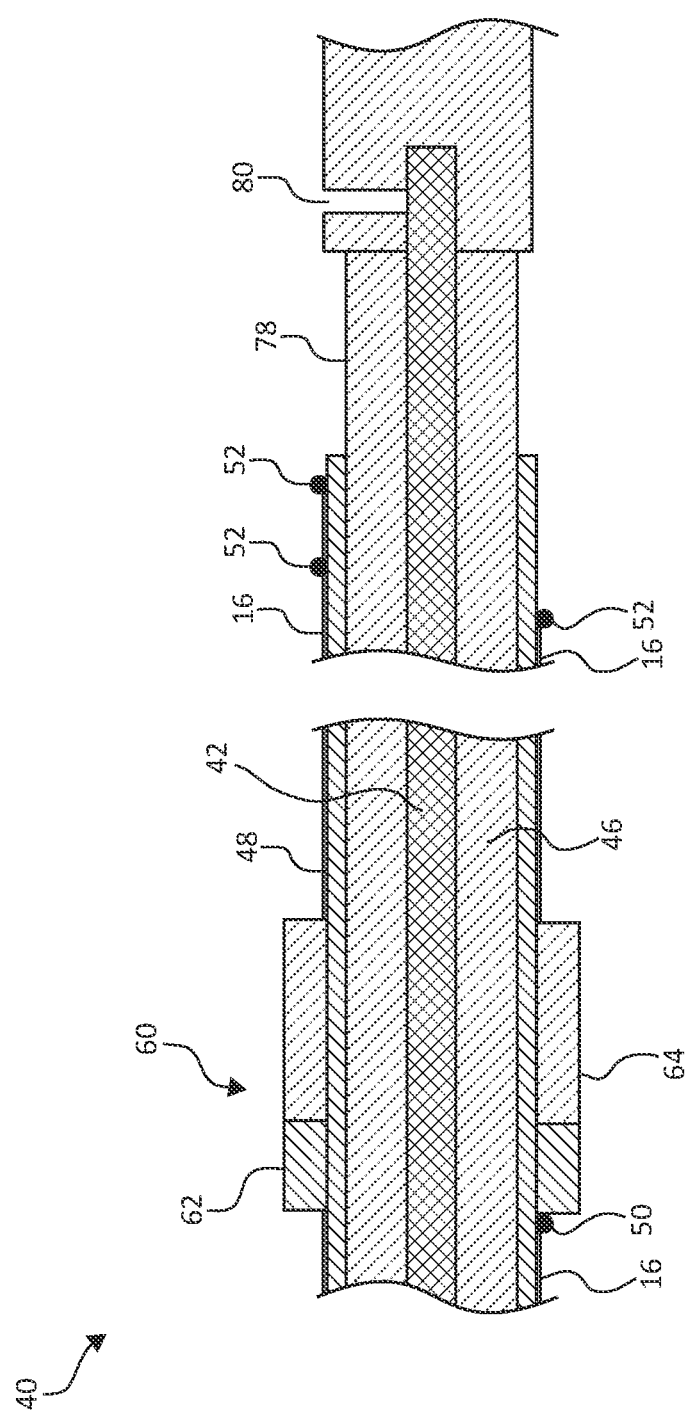
FIG. 9 is an enlarged, cross-sectional view of a portion of a feedline of a probe assembly depicting a plurality of temperature sensors in accordance with an embodiment of the present disclosure.

FIG. 9 illustrates another embodiment including a plurality of temperature sensors. In this embodiment, the first temperature sensor 50 is disposed at an axial location proximate the proximal portion of the balun short 62, the distal portion of the balun short 62 or the distal portion of the balun insulator 64, while a plurality of second temperature sensors 52 may be disposed distal to the balun 60 and proximal to the feedgap 78. According to an embodiment, the second temperature sensors 52 may be arranged in an array. For example, the plurality of the second temperature sensors 52 may be arranged at approximately 0.8 inch (20.32 mm), 1.0 inch (25.4 mm), 1.2 inches (30.48 mm), and 1.4 inches (35.56 mm) from the distal tip 12 of the microwave ablation device 10. By using the second temperature sensors 52 and the first temperature sensor 50, a thermographic profile of the tissue can be created for review and analysis during and after the procedure, a progression of the treatment may be monitored, and/or a terminal threshold of the treatment may be monitored to end the treatment. In an embodiment, the first temperature sensor 50 and the second temperature sensors 52 may detect rising temperatures of an ablation zone, which may be correlated with ablation growth in the surrounding tissue.

The feedline 40 may be manufactured using any one of numerous suitable processes. Generally, a conductive wire is provided to serve as the inner conductor 42. The conductive wire may be drawn or extruded to thereby form the inner conductor 42, which may serve as a core or center of the feedline 40. The dielectric material 46 is used to coat and thereby encapsulate the inner conductor 42, for example, by extrusion, at a secured position to form the dielectric material 46. The outer conductor 48 is then formed over the dielectric material 46. In an embodiment, a conductive material is placed around the dielectric material 46 to form the outer conductor 48, for example, by inserting the dielectric material 46, which may be shaped as a tube, or by wrapping the conductive material around the dielectric material 46.

The temperature sensor 50 is positioned adjacent the outer conductor 48. In an embodiment, a thermocouple forming a portion of the temperature sensor 50 is disposed at a desired position over a surface of the outer conductor 48, and an associated transmission line 16, which extends proximally from the thermocouple 50, is disposed such that it runs along a length of the outer conductor 48 and extends past its proximal end. The proximal ends of the inner conductor 42, the dielectric material 46, and the outer conductor 48 are aligned, such that the transmission line 16 extends past all the proximal ends of the inner conductor 42, the dielectric material 46, and the outer conductor 48.

In another embodiment in which multiple temperature sensors are included, thermocouples of each temperature sensor, for example, a first temperature sensor 50 and one or more second temperature sensors 52, are disposed at a desired position, and transmission lines 16 corresponding to each are placed along a length of the outer conductor 48 to extend past a proximal end thereof. Dielectric material 46 surrounds the inner conductor 42, for example, by extrusion. In another embodiment, the inner conductor 42 is coated with the dielectric material 46. In either case, conductive material is disposed over the inner conductor 42 and dielectric material 46 to form the outer conductor 48. The first temperature sensor 50, the one or more second temperature sensor 52, and the transmission line 16 are then secured to the outer conductor 48. The temperature sensors 50, 52 are positioned as desired.

Once manufactured, the feedline 40 and temperature sensor 50 may be further processed. For example, in an embodiment, the balun 60 is coupled to the outer conductor 48 by any suitable means at any desired location, such as proximate to the first temperature sensor 50, between the first temperature sensor 50 and the second temperature sensor(s) 52.

During operation, probe assembly 11 with the embedded temperature sensor 50 will monitor the temperature of components of the probe assembly 11 and propagate a signal that relays the measured temperature to the microwave ablation device 10, which will regulate the temperature to prevent damage to components of the probe assembly 11, and/or prevent harm to the clinician or patient.

Various embodiments of the present disclosure provide a probe assembly including an embedded temperature sensor, a balun, and a feedline. Embodiments may be suitable for utilization with hand-assisted, endoscopic, and laparoscopic surgical procedures such as Video Assisted Thoracic Surgery. Embodiments may be implemented using electromagnetic radiation at microwave frequencies, RF frequencies or at other frequencies. A microwave ablation device including the presently disclosed probe assembly is configured to operate at frequencies between about 300 MHz and about 10 GHz.

Various embodiments of the presently disclosed probe assembly including a temperature sensor, a balun, and a feedline are suitable for microwave or RF ablation and for use to pre-coagulate tissue for microwave or RF ablation-assisted surgical resection. Although various embodiments described hereinbelow are disclosed to perform microwave ablation and the complete destruction of target tissue, it is to be understood that embodiments for directing electromagnetic radiation may be used with other therapies in which the target tissue is partially destroyed or damaged, such as, for example, to prevent the conduction of electrical impulses within heart tissue. In addition, although the following description describes the use of a dipole microwave antenna, the teachings of the present disclosure may also apply to a monopole, helical or other suitable type of microwave antenna or RF electrode.

As it is used in this description, "ablation procedure" generally refers to any ablation procedure, such as, for example, microwave ablation, radiofrequency (RF) ablation, or microwave or RF ablation-assisted resection.

As it is used in this description, "length" may refer to electrical length or physical length. In general, electrical length is an expression of the length of a transmission medium in terms of the wavelength of a signal propagating within the medium. Electrical length is normally expressed in terms of wavelength, radians or degrees. For example, electrical length may be expressed as a multiple or submultiple of the wavelength of an electromagnetic wave or electrical signal propagating within a transmission medium. The wavelength may be expressed in radians or in artificial units of angular measure, such as degrees. The electrical length is in general different from the physical length. By the addition of an appropriate reactive element (capacitive or inductive), the electrical length may be made significantly shorter or longer than the physical length.

This description may use the phrases "in an embodiment," "in embodiments," "in some embodiments," or "in other embodiments," which may each refer to one or more of the same or different embodiments in accordance with the present disclosure.

Although embodiments have been described in detail with reference to the accompanying drawings for the purpose of illustration and description, it is to be understood that the inventive processes and apparatus are not to be construed as limited thereby. It will be apparent to those of ordinary skill in the art that various modifications to the foregoing embodiments may be made without departing from the scope of the disclosure.

What is claimed is:

1. A microwave ablation device, comprising:
    a cable assembly configured to connect to an energy source;
    a feedline in electrical communication with the cable assembly, the feedline defining a longitudinal axis and including a first temperature sensor disposed at a first axial location of the feedline, the first temperature sensor extending along a length of the feedline and configured to sense a temperature at the first axial location;
    a handle assembly having an upper portion defined on a first side of the longitudinal axis and a lower portion defined on a second side of the longitudinal axis opposite to the first side;
    a transition assembly at least partially disposed within the handle assembly and coupling the feedline to the cable assembly, the transition assembly having a first portion extending longitudinally along the longitudinal axis and a second portion extending transverse to the longitudinal axis and exiting the handle assembly at the lower portion of the handle assembly; and
    a wire extending from the first temperature sensor and disposed parallel and in contact with an outer conductor of the feedline, the wire extending from the feedline through the upper portion of the handle assembly to a first location in the upper portion of the handle assembly that is proximal to a proximal-most end of the feedline, and from the first location across the longitudinal axis into a second location in the lower portion of the handle assembly that is proximal to the proximal-most end of the feedline, wherein the wire exits the handle assembly from the second location and extends within the cable assembly to a connector assembly disposed at a proximal end of the cable assembly, wherein the wire extends continuously from the first temperature sensor to the connector assembly via the feedline, the first and second locations, and the cable assembly.

2. The microwave ablation device of claim 1, further comprising a balun disposed on the outer conductor, wherein the first temperature sensor is disposed proximate to the balun.

3. The microwave ablation device of claim 2, further comprising an antenna assembly electrically connected to the feedline and positioned distal to the balun, the antenna assembly including:
    a proximal radiating section disposed proximate to the balun;
    a distal radiating section disposed distal to the proximal radiating section; and
    a feedgap disposed between the proximal radiating section and the distal radiating section, wherein the first temperature sensor is disposed proximal to the balun.

4. The microwave ablation device of claim 2, further comprising an antenna assembly electrically connected to the feedline and disposed distal to the balun, the antenna assembly including:
    a proximal radiating section disposed proximate to the balun;
    a distal radiating section disposed distal to the proximal radiating section; and
    a feedgap disposed between the proximal radiating section and the distal radiating section, wherein the first temperature sensor is disposed distal to the balun and proximal to the feedgap.

5. The microwave ablation device of claim 4, wherein the feedline further includes an inner conductor and a dielectric material disposed between the inner conductor and the outer conductor, the first temperature sensor being disposed on the outer conductor and the outer conductor extending coaxially with the inner conductor.

6. The microwave ablation device of claim 5, wherein the feedline further includes a second temperature sensor disposed at a second axial location along the length of the feedline and configured to sense a temperature at the second axial location, the first temperature sensor being disposed proximal to the second temperature sensor.

7. The microwave ablation device of claim 5, wherein the feedline further includes a plurality of second temperature sensors each disposed at a different axial locations along the length of the feedline and configured to sense a temperature at the different axial locations, the first temperature sensor being located proximal to the plurality of second temperature sensors.

8. The microwave ablation device of claim 7, wherein the plurality of second temperature sensors is arranged in an array.

* * * * *